US 8,777,998 B2

(12) United States Patent
Daniels et al.

(10) Patent No.: US 8,777,998 B2
(45) Date of Patent: Jul. 15, 2014

(54) PEDIATRIC LONG BONE SUPPORT OR FIXATION PLATE

(75) Inventors: David Daniels, Winona Lake, IN (US); Dave Bailey, South Bend, IN (US); Chris Bremer, Warsaw, IN (US); Daniel Hoernschemeyer, Columbia, MO (US)

(73) Assignee: Orthopediatrics Corp., Warsaw, IN (US)

( * ) Notice: Subject to any disclaimer, the term of this patent is extended or adjusted under 35 U.S.C. 154(b) by 1214 days.

(21) Appl. No.: 12/390,834

(22) Filed: Feb. 23, 2009

(65) Prior Publication Data
US 2010/0217332 A1 Aug. 26, 2010

(51) Int. Cl.
*A61B 17/88* (2006.01)
*A61B 17/80* (2006.01)

(52) U.S. Cl.
USPC .............. 606/280; 606/286; 606/291

(58) Field of Classification Search
USPC ............ 606/70, 71, 280, 286, 291, 305
See application file for complete search history.

(56) References Cited

U.S. PATENT DOCUMENTS

| 5,190,544 | A | 3/1993 | Chapman et al. | |
|---|---|---|---|---|
| 5,772,662 | A | 6/1998 | Chapman et al. | |
| 6,183,475 | B1 * | 2/2001 | Lester et al. | 606/281 |
| 6,623,486 | B1 * | 9/2003 | Weaver et al. | 606/281 |
| 6,712,073 | B2 | 3/2004 | Manderson | |
| 7,052,499 | B2 | 5/2006 | Steger et al. | |
| 7,090,676 | B2 * | 8/2006 | Huebner et al. | 606/71 |
| 7,137,987 | B2 | 11/2006 | Patterson et al. | |
| 7,335,204 | B2 | 2/2008 | Tornier | |
| 2002/0156474 | A1 * | 10/2002 | Wack et al. | 606/69 |
| 2004/0116930 | A1 | 6/2004 | O'Driscoll et al. | |
| 2004/0167522 | A1 | 8/2004 | Niederberger et al. | |
| 2005/0021033 | A1 | 1/2005 | Zeiler | |
| 2005/0234472 | A1 * | 10/2005 | Huebner | 606/104 |
| 2006/0129151 | A1 * | 6/2006 | Allen et al. | 606/69 |
| 2006/0173458 | A1 | 8/2006 | Forstein | |
| 2007/0270849 | A1 | 11/2007 | Orbay et al. | |
| 2008/0300637 | A1 | 12/2008 | Austin | |

FOREIGN PATENT DOCUMENTS

FR 2 406 429 5/1979

OTHER PUBLICATIONS

Search report for PCT/US2010/024970; Sep. 27, 2010.
Supplementary search report for EP 10744450; May 24, 2013.
Written opinion for PCT/US2010/024970; Sep. 27, 2010.

* cited by examiner

*Primary Examiner* — Nicholas Woodall
*Assistant Examiner* — Christine Nelson
(74) *Attorney, Agent, or Firm* — Woodard, Emhardt, Moriarty, McNett & Henry LLP

(57) ABSTRACT

Among other things, there is disclosed an orthopedic plate system for use in supporting or stabilizing long bones in pediatric patients. The plate includes a substantially planar portion for placement along a diaphysis of a long bone and a portion curved out of the plane of the planar portion for placement along at least part of a metaphysis of the long bone. Holes through the plate are provided for screws in both the curved and planar portions, which hold the plate to the long bone. The holes are substantially parallel to each other and substantially perpendicular to the plane of the planar portion. Screws through the holes and into the bone are substantially parallel to an epiphyseal plate of the long bone, so that attachment of the plate to the bone does not adversely affect growth of the long bone.

30 Claims, 5 Drawing Sheets

PEDIATRIC LONG BONE SUPPORT OR FIXATION PLATE

The present disclosure concerns implantable plates useful in pediatric cases where support or fixation of parts of a long bone are indicated.

BACKGROUND

In the field of orthopedic treatment of the long bones (e.g., femur, tibia, fibula, humerus, radius, ulna), there are a number of devices and treatments for breaks or other trauma. Among these, the uses of plate and screw systems for internal fixation of fractures is known. For example, U.S. Pat. No. 6,623,486 to Weaver shows a plate configured for attachment at an end of a long bone, with an end portion of the plate wrapping around the epiphysis of the bone. Such plates may be placed with one part alongside the long bone, straddling a break or other trauma, with screws inserted through the plate and into the bone on either side of the trauma. The bone is thus supported in a position that will allow healing, with stresses on the bone transferred via the screws to the plate.

Pediatric orthopaedic surgeons have been challenged for years when it comes to having implants for use in children or young adults (referred to herein as "pediatric" patients). Many have tried to modify small adult implants by various means, particularly plates for rigidly fixing fractures, osteotomies, etc. Such modifications are necessary to try to accommodate the variability in shape and size of the growing skeleton, even though they can potentially compromise the mechanical properties of the implant.

SUMMARY

The inventors have found that particular difficulties can arise when trying to adapt implants for adults to pediatric cases. These include the accommodation of the growth structures in pediatric bones. For example, in the case of femoral plates used for the fixation of distal femoral fractures and osteotomies, there is an additional and very significant problem involving the distal femoral growth plate of a pediatric bone. If a surgeon takes a plate that is straight and tries to contour it to fit on the distal femoral metaphysis, such contouring also re-directs the distal screw holes such that screws through those distal holes run the risk of entering and violating the distal femoral growth plate. If not recognized, such a violation could lead to a partial growth arrest in the pediatric bone with the development of deformity of the distal femur depending on which part of the growth plate is violated.

In pediatric patients, the epiphyseal plate (or "growth plate") in each long bone remains active. Responsible for longitudinal growth of the long bones, the epiphyseal plate is a cartilaginous region that generates new bone cells which stack facing the ephiphysis of the bone, with older cells being pushed toward the diaphysis. Those older cells ossify to form new bone. As one approaches the mid-twenties, the epiphyseal plate's cartilaginous cells cease their activity and slowly ossify, and the bones cannot grow any further.

With the activity of the epiphyseal plates, implant plates may be contraindicated for fear of impinging on the epiphyseal plate and consequent retarding, arresting or changing the growth of the bone. If used, such plates require great care in order not to damage the epiphyseal plate or arrest the growth of the bone. Plates that are made for adults, with a curved end to extend into the epiphysis of the bone, rely on screws placed into both the diaphysis and the epiphysis. In many cases, screws through the end of the plate extend through the epiphyseal plate and into the epiphysis. The screws keep the bone from lengthening, which may result in impeding or blocking generation of new cells by the epiphyseal plate, or in forcing newly generated cells to the side of the long bone. In either case, further growth of the bone is halted or limited, and/or continued growth may dislodge screws or otherwise cause the implant to fail. In an effort to avoid intersection of screws with an epiphyseal plate, shorter screws have been used in these situations. However, the shorter screws potentially compromise the rigidity and stability of the plate and the fixation of the bone (e.g. a distal femoral fragment).

The inventors have found cases in which a surgeon will use an adult plate to fix a pediatric long bone, and in doing so will purposefully re-orient a screw in a plate hole, cross-threading the head of the screw in it, to try to ensure that the screw does not interfere with the ephiphyseal plate. This solution has several drawbacks. Among them are the difficulty in cross-threading a screw into a hole and maintaining it in a desired orientation, the likelihood of leaving a significant portion of the screw head above the plate (and the associated likelihood of leaving a significant portion of the threaded shaft out of the bone), and the weakening of the threads in the screw head and the hole which may lead to attachment failure. Further, in many cases the plate is to be removed after the bone heals, and cross-threaded screws will be very difficult to remove.

Consequently, there are provided embodiments of plates for pediatric use on long bones which meet these needs. In certain embodiments, an apparatus for supporting a pediatric long bone includes an elongated plate having a planar portion for attachment to a diaphysis of a long bone, and a curved portion for attachment to a metaphysis of the long bone. The plate has a top surface that faces away from the long bone when the plate is implanted, the top surface being smoothly continuous between the planar portion and the curved portion. The top surface in the planar portion is in a plane and it curves out of the plane in the curved portion. The plate has a set of holes including a first plurality of holes in the planar portion, each of which has a respective central longitudinal axis that is perpendicular to the top surface, and also including a second plurality of holes in the curved portion, each of which has a respective central longitudinal axis that is not perpendicular to the top surface. The respective axes of the holes of the first plurality and the second plurality are parallel. One or all of the holes may be conical and/or threaded.

A plurality of bone screws may be provided, each for insertion through a respective one of the holes and into the bone. The screws have a shaft with a thread adapted for secure threading into the bone and a head. In embodiments in which the holes are conical and/or threaded, the heads of the screws may have a conical exterior and/or an exterior thread. If both the shaft and the head are threaded, the respective threads may have differing profiles (e.g. differing pitches) from each other. For instance, the shaft thread may have a pitch that is an integer multiple of the pitch of the head thread. The shaft length and the head length may be in a ratio the same as or a multiple of the ratio of the shaft-thread pitch to the head-thread pitch. The planar portion of the plate may include a lateral curve while remaining in or along a plane. The plate has two ends, one in the planar portion and a second end having a planar upper surface that intersects the plate's top surface in its curved portion. The second end has first and second holes for bone screws that are laterally separate from each other, and that each have a respective central longitudinal axis that is perpendicular to the planar upper surface of the second end and parallel to the central longitudinal axes of the first and second pluralities of holes. The holes of the second end may have internal threading for locking screws therein, and a line connecting the central longitudinal axes of those holes may be perpendicular to a line connecting the central longitudinal axes of two of said second plurality of holes.

In other embodiments, an apparatus for supporting a long bone in a pediatric patient includes a one-piece plate for fixation to the long bone and having a first portion within or along a plane and a second portion curving out of said plane. A first plurality of holes through the first portion each have a respective central longitudinal axis and a second plurality of holes through the second portion each have a respective central longitudinal axis, and all of the central longitudinal axes are parallel to each other and perpendicular to the plane of the first portion. A plurality of screws adapted to be placed in respective ones of the holes are provided, so that when the screws are placed in respective ones of the holes, the screws are parallel to each other and substantially perpendicular to a longitudinal axis of the long bone, and substantially parallel to an epiphyseal plate of a pediatric long bone when implanted.

The curve of the second portion may generally correspond to at least part of the curve in a metaphysis of the pediatric bone, and the first portion may be adapted to lie along a diaphysis of the pediatric bone. The curved portion, in some embodiments, includes an end having an upper surface substantially parallel to the plane of the first portion, so that the end portion does not follow the curve of the curved portion. At least one hole in the end surface of the curved portion may be among the second plurality of holes. In particular embodiments, the second plurality of holes includes two holes in the end surface of the curved portion, and a line connecting the centers of those holes in the end surface is substantially perpendicular to a line connecting the centers of others in the second plurality of holes. The holes in the plate may each have a respective conical interior, and the screws may each have a respective conical head corresponding to the respective conical interiors. In particular embodiments, the respective conical interiors and respective conical heads are conical in their entireties. The holes in the plate may each have a respective threaded interior, and the screws may each have a respective threaded head corresponding to the respective threaded interiors. The screws may each have a respective threaded head and a respective threaded shaft, and the thread on the shaft can have a pitch that is an integer multiple of a pitch of the thread on the head.

The present disclosure also includes an orthopedic plate for supporting a bone in a pediatric patient that includes a planar portion within or along a plane, a curved portion curved out of the plane, and a plurality of holes. At least one of the holes is in the planar portion and at least one is in the curved portion. The holes are adapted to accept bone screws therethrough for attaching the plate to the pediatric bone, and each of the holes has a respective central longitudinal axis. Each of the respective central longitudinal axes is substantially parallel to the others and substantially perpendicular to the plane. Such a plate can be monolithic, with the holes configured so that when the plate is placed against the bone so that its planar portion is along a diaphysis and its curved portion is along at least a portion of a metaphysis of the bone, the central longitudinal axes are substantially parallel to an epiphyseal plate of the bone.

DESCRIPTION OF THE ILLUSTRATED EMBODIMENT

Figure 1:
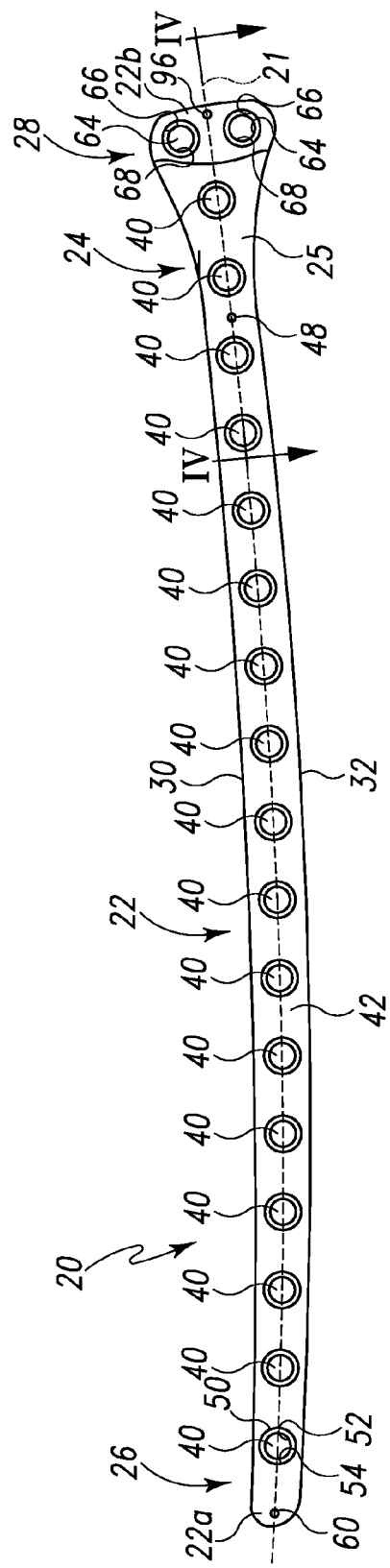
FIG. 1 is a top view of an embodiment of a bone plate useful in pediatric orthopedic cases.

For the purposes of promoting an understanding of the principles of the disclosure, reference will now be made to the embodiment illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein, being contemplated as would normally occur to one skilled in the art to which the disclosure relates.

Referring now generally to the Figures, a plate 20 useful in repairing fractures in or supporting bones, particularly long bones such as the femur, tibia, humerus or others, is shown. The illustrated embodiment of plate 20 is particularly useful in pediatric cases.

Figure 2:
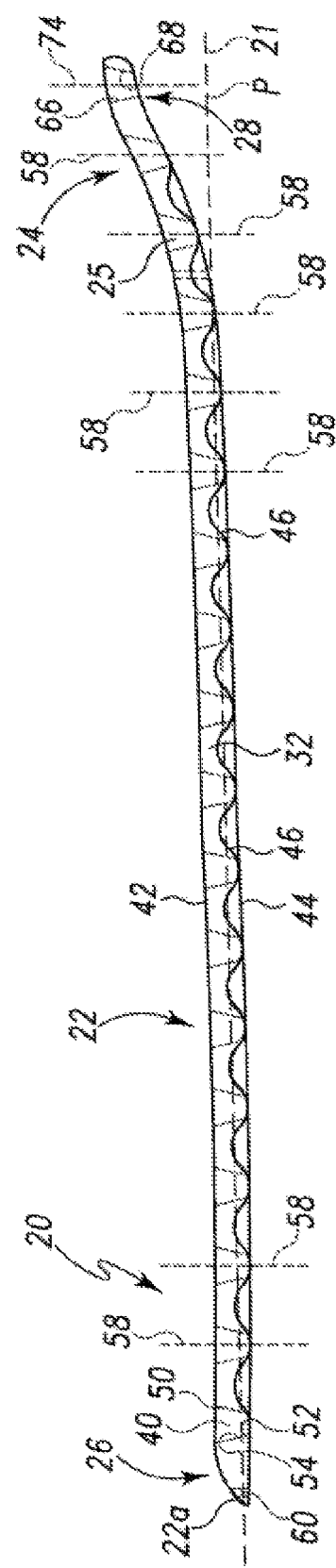
FIG. 2 is a side elevational view of the embodiment shown in FIG. 1.
Figure 3:
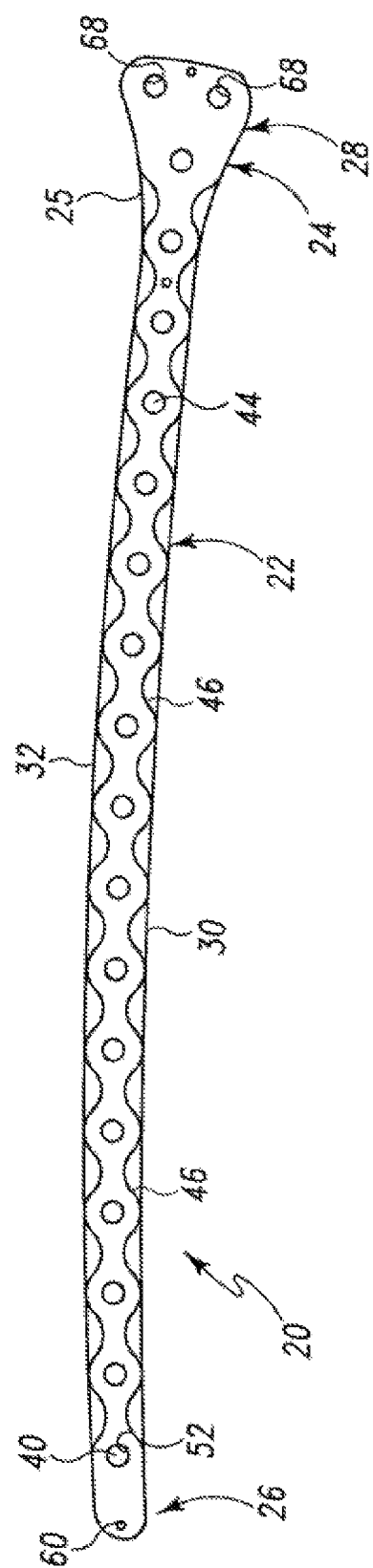
FIG. 3 is a bottom view of the embodiment shown in FIG. 1.
Figure 4:
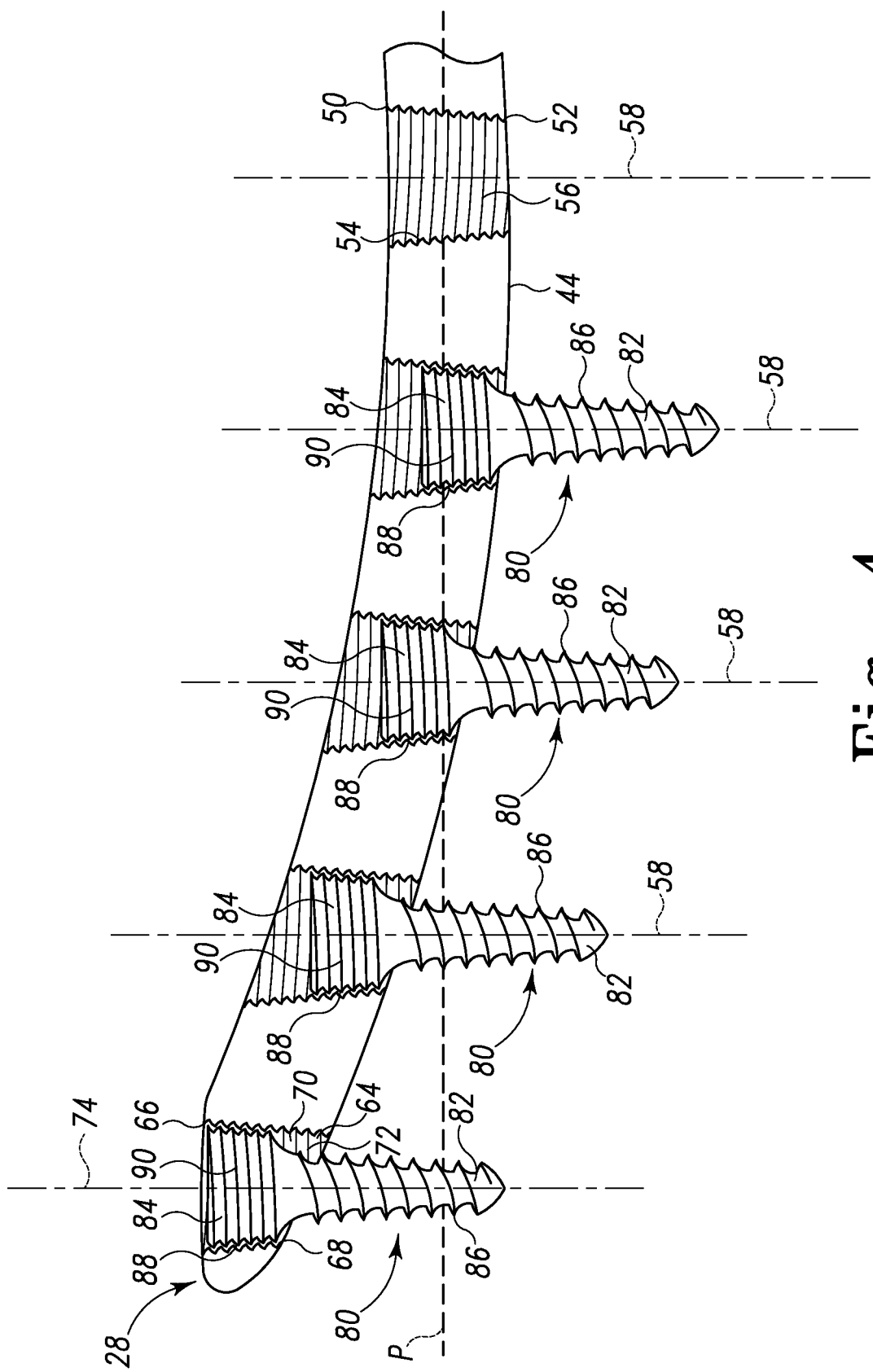
FIG. 4 is a cross-sectional view of the embodiment shown in FIG. 1, taken along the lines IV-IV and viewed in the direction of the arrows.

The illustrated embodiment of plate 20 is a one-piece device that is generally linear so as to be effectively attached to the diaphysis and metaphysis of a long bone. Plate 20 is at least substantially planar (i.e. in or along the page as seen in FIG. 1, or within or along plane P seen in FIG. 2) for most of its length, but also has a curve out of plane P as it approaches one end. A central longitudinal axis 21 extends through the planar portion of plate 20 within plane P. Plate 20 is thus within or along plane P at some points, and rises out of plane P (e.g. FIG. 2) as its end curves upwardly or outwardly. The planar portion 22 generally aligns with and is able to be closely attached to the shaft or diaphysis of a long bone, and the outwardly-curved portion 24 relates to the curve in the long bone from the diaphysis into or along the metaphysis. A neck 25 in plate 20 begins curved portion 24 or is between curved portion 24 and planar portion 22.

Plate 20 is elongated, having a first end 26 adjacent or within first portion 22 and a second end 28 adjacent or within second portion 24, and lateral edges or sides 30, 32 opposite each other and extending from end 26 to end 28. Axis 21 is equidistant from edges 30 and 32 along portion 22 of plate 20. The elongation of plate 20 results in sides 30, 32 having a length between ends 26, 28 much greater than the width measured between sides 30, 32. The length L in this embodiment allows plate 20 to extend along enough of the diaphysis to bridge a fracture, osteotomy, or other trauma, excision or deformation, or to get sufficient purchase on the diaphysis, when curved portion 24 is fitted into the curve at the diaphysis/metaphysis junction of the bone. In the illustrated embodiment, the width between sides 30, 32 is relatively small, just large enough to accommodate screw holes 40. Such a limited width makes plate 20 particularly useful in pediatric indications, in which bones of small width compared to adult long bones are present.

Plate 20 has an upper surface 42 and a lower surface 44 between edges 30, 32. Lower surface 44 contacts or faces the bone, and upper surface 42 faces away from the bone, when plate 20 is implanted. Upper surface 42 is substantially or completely planar in one embodiment, and may also be configured with a slight convex curvature as viewed from end 26, i.e., a plane through plate 20 between a pair of holes 40 and perpendicular to longitudinal axis 21 will intersect upper surface 42 in an arc upwardly convex (as viewed in FIG. 2). Lower surface 44 includes a series of convex indentations 46, each indentation 46 being between a pair of holes 40 and along an edge 30 or 32. Lower surface 44 in this embodiment is also slightly concave as viewed from end 26, i.e., a plane through plate 20 between a pair of holes 40 and perpendicular to its longitudinal axis will intersect lower surface 44 in a concave arc. The concave arc corresponds generally to the exterior curvature around the long axis of the diaphysis, allowing closer fit of plate 20 to the bone. Indentations 46 reduce the weight of plate 20 while retaining support strength, and they allow less of lower surface 44 to contact the bone, resulting in less limitation of blood flow or damage to bone tissue.

The illustrated embodiment of plate 20 also includes a slight lateral curvature, so that (as viewed in FIG. 1) plate 20 bends slightly to the left as one moves from end 26 toward end 28 along plate 20. The lateral curvature does not move planar portion 22 out of plane P, and is allows plate 20 to attach in a more advantageous position relative to bone features, and/or gives plate 20 additional strength and opposition to twisting or bending of plate 20 after attachment. It will be appreciated that "lateral" as used here indicates a direction perpendicular to the curvature of curved portion 24, or a direction essentially tangent to the diaphysis of the bone to which plate 20 is attached, as opposed to perpendicularly away from the diaphysis. It will further be appreciated that a similar lateral curvature to the right, or no lateral curvature at all, can be provided in other embodiments.

A plurality of holes 40 for accommodating bone screws is provided along the length of plate 20 in this embodiment, a first plurality of holes 40 being in planar portion 22 and a second plurality of holes 40 being in curved portion 24, including neck 25. In the illustrated embodiment, holes 40 are equally-spaced from each other along plate 20 from a point adjacent end 26 to a point adjacent end 28. With that arrangement, the surgeon has a large selection of holes 40 to use when implanting plate 20, and can therefore secure plate 20 to the bone at one or more of a variety of locations so as to ensure a strong connection and the desired degree of (or no) encroachment by screws on locations where healing is to occur.

In the illustrated embodiment, each of holes 40 is identically configured as a cone, having an upper opening 50 in upper surface 42 and a lower opening 52 in lower surface 44, with lower opening 52 having a smaller diameter than the respective upper opening 50. Each hole 40 has a conical side wall 54 in which a female thread 56 is cut, and a central axis 58 through its upper opening 50 and lower opening 52. In this particular embodiment, central axes 58 of holes 40 are parallel to each other, and are perpendicular to upper surface 42 in planar portion 22 of plate 20. Central axes 58 of holes 40 in curved portion 24 are perpendicular to plane P and axis 21, though the curvature of neck 25 and portion 24 makes holes 40 in them non-perpendicular to parts of upper surface 42 and lower surface 44 that are adjacent to them.

End 26 of the illustrated embodiment includes an upper surface 22a that is slanted with respect to the rest of upper surface 22 to form a wedge. An aperture 60 that is substantially smaller than holes 40 is also provided, which extends through surface 22a. Surface 22a reduces resistance to movement of plate 20 along a guidewire through or under soft tissues in minimally-invasive (e.g. percutaneous) procedures, which may be particularly preferred in pediatric cases so as to limit damage to developing soft tissues.

Curved portion 24 of the illustrated embodiment includes or extends from neck 25 that widens plate 20 (spreading edges 30, 32 apart from each other) as one moves toward end 28. End 28 has an upper surface 22b that is at least substantially parallel to and offset from upper surface 22 in planar portion 22 (and parallel to and offset from plane P). Surface 22b does not continue the curvature of upper surface 22 in curved portion 24, and reduces resistance to movement in a similar fashion to surface 22a. End 28 and surface 22b are large enough to include two holes 64 in a side-by-side formation. Holes 64 each have an upper opening 66 through surface 22b and a lower opening 68 through surface 44, as well as a conical wall 70 with a female thread 72 cut in it. Holes 64 each have a central axis 74 through the center of their respective upper openings 66 and lower openings 68, and central axes 74 are parallel to each other and to central axes 58 of holes 40, and are also perpendicular to surface 22b and plane P. The illustrated embodiment shows that a line connecting the axes 74 of holes 64 is substantially perpendicular to a line connecting axes 58 of at least the first two holes adjacent surface 22b, and perhaps others. In the illustrated embodiment, holes 64 are configured identically to holes 40, with the exception that their overall height (measured along their central axes) is shorter because the thickness of end 28 is less than the thickness of portions 22 or 24 of plate 20.

A plurality of screws 80 are also provided for use with plate 20. In the illustrated embodiment, screw 80 is a one-piece structure that includes a shaft portion 82 and a head portion 84. Shaft portion 82 is a cylinder having an external thread 86 configure for insertion into bone. Head portion 84 is configured to be accommodated and locked in holes 40 and 64 of plate 20, and so have a conical external side surface 88 with an external thread 90. External thread 90 assists not only in placement of screw 80, but also in removal of screw 80 because of the interaction of external thread 90 with thread 56, and removal of implants is generally indicated with pediatric patients. An upper surface 92 on head 84 includes an internal print (not shown) for accommodating a driving or gripping tool (not shown), and in particular embodiments the print may be hexagonal, square, TORX®, or a similar print. Conical head 84 and shaft 82 are both centered on a longitudinal axis that aligns with the respective central longitudinal axis 58, 74 of the hole 40 or hole 64 into which the respective screw 80 is threaded. In this embodiment, screws 80 can have only one orientation relative to plate 20 because of the complementary conical configurations of holes 40, 64 and screw heads 80. In that orientation, shafts 82 of screws 80 are parallel to or along a central axis 58, 74 of their respective holes 40, 64 in which they are threaded.

As will be appreciated from the drawings, the pitch of shaft thread 86 is different from that of head thread 90 in the illustrated embodiment. Shaft thread 86 is configured for insertion into bone, and it has a crest diameter that extends out from the shaft or root by a substantial amount so as to ensure a secure purchase in bone tissue. Head thread 90, on the other hand, need not have such a crest diameter because it threads into plate 20 or another piece with its corresponding strength and rigidity. Shaft thread 86 has a given pitch (i.e., a particular number of windings per inch, or conversely a particular longitudinal distance along the shaft traveled with one revolution of the thread) that is different from the pitch of the head thread 90. In the illustrated embodiment, shaft thread 86 has a pitch that is greater than that of head thread 90—the distance traveled along the shaft by one winding is greater in the shaft thread 86 than in the head thread 90—and in a particular embodiment the pitch of shaft thread 86 is three times that of head thread 90. In that embodiment, one revolution of screw 80 about its longitudinal axis results in shaft 82 moving into bone by a given distance and head 84 moving into hole 40 (or hole 68) one-third of that distance. The overall length of shaft 82 may also be three times that of head 84, so that if threading of screw 80 into bone and into plate 20 is started at the same time, then it will also end at the same time with all of thread 86 in bone and head 84 seated in its respective hole 40 or 68. It will be appreciated that other integral multiples or relationships between the pitches of threads 86 and 90 may be used.

It will be seen that the configuration of the illustrated embodiments of plate 20 and screws 80 result in a close fit of plate 20 with the topography of a long bone such as the femur, tibia or humerus, and screws 80 are all parallel to each other, even those in neck 25 and curved portion 24. As noted, holes 40 in planar portion 22 of plate 20 are perpendicular to surface 42 of plate 20, and since surface 42 runs along the shaft of the bone (parallel to the longitudinal axis of the long bone), screws 80 are all substantially perpendicular to the longitudinal axis of the bone. Such a configuration has a number of advantages, particularly in the realm of pediatric indications.

For one thing, when the screws necessarily are parallel to each other in their normal state, any later x-ray or other image that shows non-parallel screws or screws that are not perpendicular to the longitudinal axis of the bone will be an immediate indication of a problem with healing. There is little or no need for fine comparison of a later image with a previous image to see if screws have repositioned, because the later image will immediately reveal such problems, even in the curved portion or neck of the plate.

Of particular interest to pediatric orthopedics, the disclosed configuration does not interfere with growth of the long bones. Many long bone plates wrap around and fix to the epiphysis or end of the bone, or insert one or more screws through the metaphysis and into the epiphysis, as may be appropriate for adult patients. Plate 20 does not extend on the metaphysis past the epiphyseal or "growth" plate of the bone. Screws 80 do not enter or pass through the epiphyseal plate, so that addition and ossification of bone tissue in the epiphyseal plate is not impeded. Rather, in the illustrated embodiment screws 80 in plate 20 have an orientation generally parallel to the epiphyseal plate, and generally perpendicular to the longitudinal axis of the bone. Use of a plate such as plate 20 eliminates impingement on the growth structure of a bone, as well as problems facing surgeons in trying to alter plates developed for adults to provide compatibility with a pediatric patient.

Figure 5:
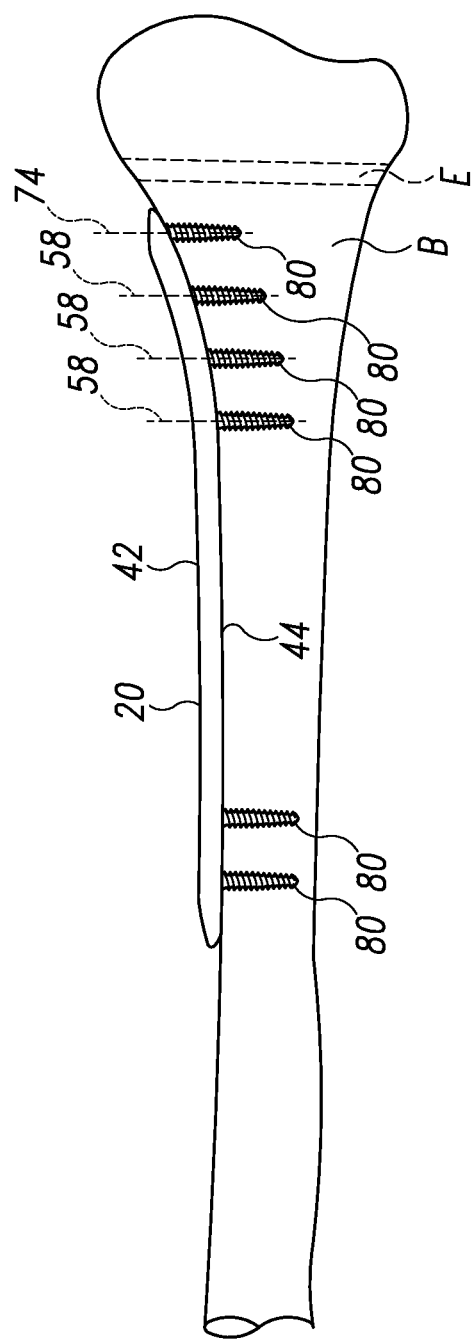
FIG. 5 is a side, part cross-sectional view of the embodiment shown in FIG. 4 attached to a long bone.

In use, plate 20 can be implanted as follows. An example concerning fixation of distal femoral fractures is indicated below, although plate 20 has application with respect to other procedures or indications. A representation of an implanted plate 20 is shown in FIG. 5 attached to a long bone B (e.g. approaching the distal or inferior end of the femur) and its epiphyseal plate E, with only six screws 80 shown for clarity. It will be understood that a different number of screws 80 may be used in attaching plate 20 to a bone, and in fact all of the holes 40, 64 of plate 20 may have a respective screw 80 threaded through it and into the bone B.

A surgical approach is made to a long bone to be implanted. The approach can be an open method, or it can be a percutaneous method. If an open method, then the necessary incisions and retraction of tissue are made to expose at least the portion of the bone having a break or other trauma or deformation. If a percutaneous method, then small openings through skin and muscle are made adjacent the implant site, guide wires are inserted and anchored, and plate 20 is inserted (e.g. by placing an anchored guide wire (not shown) through apertures 60 and 96, and moving plate 20 along the guide wire).

When plate 20 is in position over the long bone, it can be initially held in position by inserting a pin (not shown) or other temporary holder through one or more of holes 40 and/or aperture 98 and into the bone. With plate 20 temporarily held, holes are drilled into the bone for screws 80 corresponding to a number of holes 40, 64, and in some embodiments the holes are drilled through particular holes 40 and/or 64 of plate 20. In some embodiments, at least one hole is drilled in the bone on either side of a break, trauma, deformation or other therapy site in the bone, and in certain embodiments two, three or more holes are drilled on each side of the therapy site. With respect to a distal femoral fracture, in which the fracture is in the diaphysis or metaphysis near the lower extremity of the femur, holes may be drilled on either side of the fracture in the diaphysis and metaphysis. These holes will be substantially perpendicular to the longitudinal axis of the diaphysis, and substantially parallel to the epiphyseal plate, in keeping with the above discussion.

After drilling one or more holes as noted above, a screw 80 is threaded into respective bone holes through respective holes 40 or 64 in plate 20. Once at least one screw 80 is threaded into a bone hole on either side of the therapy site, temporary fixation pins (if any have been used) may be removed, since the placed screws 80 maintain plate 20 in the desired location. Each screw 80 is threaded into the bone and into plate 20 so that most or all of shaft 82 is within bone (i.e. plate 20 is very close to or contacting the surface of the bone), and so that head 84 is seated and locked in its respective hole 40 or 64. Head 84 can be threaded into plate 20 until its conical surface 88 engages or wedges into the conical surface of its respective hole 40 or 64. In the case of a distal femoral fracture, one or more screws may be threaded into holes 64 in curved portion 24 and into the metaphysis, and one or more screws may be threaded into holes 40 in planar portion 22 and into the diaphysis. The screws in the metaphysis are substantially perpendicular to the longitudinal axis of the diaphysis, and substantially parallel or at least non-intersecting with the epiphyseal plate. The screws in the diaphysis are also substantially perpendicular to the longitudinal axis of the diaphysis, parallel to the screws in the metaphysis. Plate 20 bridges a fracture or holds together separated parts of the distal femur, to support the bone while healing takes place.

Once the desired number of screws 80 are inserted, or all of holes 40 and 64 of plate 20 are occupied by a respective screw 80, additional steps may be performed (e.g. placement of bone cement, osteoinductive compositions, or other therapeutic agents or implants), or the surgery may be concluded. In a percutaneous approach, remaining guide wire(s) are removed and incisions closed. In an open approach, retraction of tissues is eliminated and repair of tissues and closing of incisions is performed.

The illustrated embodiment of plate 20 and screws 80 show that screws 80 have only one orientation with respect to plate 20 because of either of both of the complementary conical and/or threaded surfaces of head 84 of screw 80. That orientation is one in which each screw 80 is parallel to the respective axis 58, 74 of the hole 40, 68 in which it is inserted. In a particular embodiment, the longitudinal axis of the screw 80 coincides with the axis 58, 70 of the hole 40, 68. With each screw 80 parallel to its respective axis 58, 74, it follows that each of the screws 80 is parallel to the other screws 80 when they have been inserted into plate 20. As noted above, axes 58 are perpendicular to plane P and axis 21 and upper surface 42 in the planar portion 22 of plate 20, and axis 21 is at least substantially parallel to the central longitudinal axis of a long bone when portion 22 of plate 20 is placed against and along the diaphysis of the long bone. When plate 20 is attached to bone B, each of screws 80 is at least substantially perpendicular to the central longitudinal axis of bone B. Screws 80 in holes 74, in the illustrated embodiment, can only be oriented substantially perpendicular to the central longitudinal axis of bone B and substantially parallel to the epiphyseal plate, and cannot be inserted into or through the epiphyseal plate.

For better compatibility with pediatric long bones, the illustrated embodiment of plate 20 has one line of holes along the center of plate 20. The single line fits with the relative narrowness of pediatric long bones while also making plate 20 easier to use for the surgeon, since it requires only one orientation of screws.

Plate 20 and screws 80 may be made of a variety of sturdy biocompatible materials, most notably metals such as titanium or stainless steel. These materials provide the strength needed to support the long bones, particularly in growing children. Other sturdy materials may be used, such as certain hard plastics or ceramics.

The illustrated embodiment shows a combination of locking screws in a plate configured to be especially useful in pediatric cases. It will be seen that in other embodiments, some of holes 40 may be differently configured. For example, some of the holes 40 may be unthreaded or have other characteristics. It is preferable, however, to have locking screws (e.g. those with conical heads that fit closely in a complementary conical hole in a plate, and that are oriented as described above, to provide both secure locking and assured orientation of the screws for better support and protection for the patient.

While embodiments have been illustrated and described in detail in the drawings and foregoing description, the same is to be considered as illustrative and not restrictive in character, it being understood that only those embodiments have been shown and described and that all changes and modifications that come within the spirit of the disclosure are desired to be protected.

What is claimed is:

1. An apparatus for supporting a pediatric bone whereby the apparatus would not interfere with growth in the epiphyseal plate of the pediatric patient, comprising:
an elongated plate having a planar portion for attachment to a diaphysis of a pediatric bone, and a curved portion for attachment to a metaphysis of the pediatric bone, said plate having a top surface that faces away from the bone when said plate is implanted, said top surface being smoothly continuous between said planar portion and said curved portion and being in a plane in said planar portion and curved out of said plane in said curved portion;
wherein said plate has a set of holes, said set including a first plurality of holes in said planar portion, each of said first plurality of holes having a respective central longitudinal axis that is perpendicular to said top surface, and said set also including a second plurality of holes in said curved portion, each of said second plurality of holes having a respective central longitudinal axis that is not perpendicular to said top surface, and wherein said respective axes of said holes of said first plurality and said second plurality are parallel.

2. The apparatus of claim 1, wherein at least one of said holes is conical and threaded.

3. The apparatus of claim 1, wherein all of said holes are conical and threaded.

4. The apparatus of claim 3, further comprising a plurality of bone screws each for insertion through a respective one of said holes and into the bone, said screws having a shaft with a first thread adapted for secure threading into the bone and a head, said head having a conical exterior and a second thread in said conical exterior, said second thread having a different profile from that of said first thread.

5. The apparatus of claim 4, wherein said first thread has a first pitch and said second thread has a second pitch, and said first pitch is an integer multiple of said second pitch.

6. The apparatus of claim 4, wherein said first thread has a first pitch and said second thread has a second pitch, and said shaft has a first length and said head has a second length, and the ratio of said first length to said second length is an integer multiple of the ratio of said first pitch to said second pitch.

7. The apparatus of claim 1, wherein said planar portion includes a lateral curve.

8. The apparatus of claim 7, wherein the planar portion includes a central longitudinal axis, and at least part of said axis has said lateral curve.

9. The apparatus of claim 8, wherein the central longitudinal axis intersects the centers of at least two of the first plurality of holes and of at least two of the second plurality of holes.

10. The apparatus of claim 1, wherein when said plate is implanted on the pediatric bone said axes of said second plurality of holes are parallel to an epiphyseal plate of the bone.

11. The apparatus of claim 1, wherein said second plurality of holes is located so that they are to the diaphysis side of and non-overlapping with an epiphyseal plate when the apparatus is implanted.

12. The apparatus of claim 11, further comprising a plurality of screws each associated with a respective one of said second plurality of holes, wherein the screws do not enter an epiphyseal plate when implanted.

13. The apparatus of claim 1, wherein said plate has a first end in said planar portion and a second end, said second end having a planar upper surface that intersects said top surface in said curved portion, said second end having at least one hole for a bone screw, said at least one hole having a central longitudinal axis that is perpendicular to said planar upper surface of said second end and parallel to said central longitudinal axes of said first and second pluralities of holes.

14. An apparatus for supporting a pediatric bone, comprising:
an elongated plate having a planar portion for attachment to a diaphysis of a pediatric bone, and a curved portion for attachment to a metaphysis of the pediatric bone, said plate having a top surface that faces away from the bone when said plate is implanted, said top surface being smoothly continuous between said planar portion and said curved portion and being in a plane in said planar portion and curved out of said plane in said curved portion;
wherein said plate has a set of holes, said set including a first plurality of holes in said planar portion, each of said first plurality of holes having a respective central longitudinal axis that is perpendicular to said top surface, and said set also including a second plurality of holes in said curved portion, each of said second plurality of holes having a respective central longitudinal axis that is not perpendicular to said top surface, and wherein said respective axes of said holes of said first plurality and said second plurality are parallel,
wherein said plate has a first end in said planar portion and a second end, said second end having a planar upper surface that intersects said top surface in said curved portion, said second end having first and second holes for bone screws, said first and second holes being laterally separate from each other, said first and second holes each having a respective central longitudinal axis that is perpendicular to said planar upper surface of said second end and parallel to said central longitudinal axes of said first and second pluralities of holes.

15. The apparatus of claim 14, wherein said first and second holes of said second end have internal threading for locking screws therein, and wherein a line connecting the central longitudinal axes of said first and second holes is perpendicular to a line connecting the central longitudinal axes of two of said second plurality of holes.

16. The apparatus of claim 14, further comprising a plurality of screws adapted to be placed in respective ones of said holes, wherein when said screws are placed in respective ones of said holes, said screws are parallel to each other and positioned to be substantially perpendicular to a longitudinal axis of the long bone and to the diaphysis side of and non-overlapping with an epiphyseal plate of the long bone.

17. An apparatus for supporting a long bone in a pediatric patient whereby the apparatus would not interfere with growth in the epiphyseal plate of the pediatric patient, comprising:
a one-piece plate for fixation to the long bone, said plate having a first portion within or along a plane and a second portion curving out of said plane, said plate having a first plurality of holes through said first portion each having a respective central longitudinal axis and a second plurality of holes through said second portion each having a respective central longitudinal axis, wherein all of said central longitudinal axes are parallel to each other and perpendicular to said plane; and
a plurality of screws adapted to be placed in respective ones of said holes, wherein when said screws are placed in respective ones of said holes, said screws are parallel to each other and positioned to be substantially perpendicular to a longitudinal axis of the long bone and to the diaphysis side of and non-overlapping with an epiphyseal plate of the long bone.

18. The apparatus of claim 17, wherein the curve of said second portion generally corresponds to at least part of the curve in a metaphysis of the long bone, and wherein said first portion is adapted to lie along a diaphysis of the long bone.

19. The apparatus of claim 17, wherein said curved portion includes an end having an upper surface substantially parallel to said plane, so that said end portion does not follow the curve of said curved portion.

20. The apparatus of claim 19, wherein said second plurality of holes includes at least one hole in said end surface of said curved portion.

21. The apparatus of claim 19, wherein said second plurality of holes includes two holes in said end surface of said curved portion, wherein a line connecting the centers of said holes in said end surface is substantially perpendicular to a line connecting the centers of others of said second plurality of holes.

22. The apparatus of claim 17, wherein said first and second plurality of holes each have a respective conical interior, and said screws each have a respective conical head corresponding to said respective conical interiors.

23. The apparatus of claim 22, wherein said respective conical interiors and respective conical heads are conical in their entireties.

24. The apparatus of claim 17, wherein said first and second plurality of holes each have a respective threaded interior, and said screws each have a respective threaded head corresponding to said respective threaded interiors.

25. The apparatus of claim 17, wherein said screws each have a respective threaded head and a respective threaded shaft, and the thread on said threaded shaft has a pitch that is an integer multiple of a pitch of the thread on said threaded head.

26. The apparatus of claim 17, wherein said plate has a first end in said planar portion and a second end, said second end having a planar upper surface that intersects said top surface in said curved portion, said second end having at least one hole for a bone screw, said at least one hole having a central longitudinal axis that is perpendicular to said planar upper surface of said second end and parallel to said central longitudinal axes of said first and second pluralities of holes.

27. An orthopedic plate for supporting a long bone in a pediatric patient whereby the apparatus would not interfere with growth in the epiphyseal plate of the pediatric patient, comprising a planar portion within or along a plane, a curved portion curved out of said plane, and a plurality of holes, at least one of said holes being in said planar portion and at least one of said holes being in said curved portion, said holes adapted to accept bone screws therethrough for attaching said plate to the long bone, wherein each of said holes has a respective central longitudinal axis, said respective central longitudinal axes being substantially parallel to each other and substantially perpendicular to said plane,
wherein said holes are located so that they are to the diaphysis side of and non-overlapping with an epiphyseal plate when the apparatus is implanted.

28. The plate of claim 27, wherein said plate is monolithic, and wherein said holes are configured so that when said plate is placed against the long bone so that said planar portion is along a diaphysis and said curved portion is along at least a portion of a metaphysis of the bone, said central longitudinal axes are substantially parallel to an epiphyseal plate of the bone.

29. The apparatus of claim 27, further comprising a plurality of screws adapted to be placed in respective ones of said holes, wherein when said screws are placed in respective ones of said holes, said screws are parallel to each other and positioned to be substantially perpendicular to a longitudinal axis of the long bone and to the diaphysis side of and non-overlapping with an epiphyseal plate of the long bone.

30. The apparatus of claim 27, wherein said plate has a first end in said planar portion and a second end, said second end having a planar upper surface that intersects said top surface in said curved portion, said second end having at least one hole for a bone screw, said at least one hole having a central longitudinal axis that is perpendicular to said planar upper surface of said second end and parallel to said central longitudinal axes of said plurality of holes.

* * * * *